United States Patent [19]

D'Agnillo et al.

[11] Patent Number: 5,606,025

[45] Date of Patent: Feb. 25, 1997

[54] HEMOGLOBIN-ENZYME COMPLEXES

[76] Inventors: Felice D'Agnillo, 2550 Place Keller, Montreal, Quebec, Canada, H4K 2T3; Thomas M. S. Chang, 165 DuBearn Street, St. Lambert, Quebec, Canada, J4S 1K9

[21] Appl. No.: 341,873

[22] Filed: Nov. 15, 1994

[51] Int. Cl.$^6$ .......................... A61K 38/42; A61K 38/54; A61K 35/14; C07K 14/805

[52] U.S. Cl. ...................... 530/385; 424/94.2; 424/94.4; 435/189; 435/192; 530/402; 530/829

[58] Field of Search .................................. 530/380, 385, 530/402, 829; 514/126, 21, 832; 435/189, 192; 424/94.2, 94.4

[56] References Cited

U.S. PATENT DOCUMENTS

| | | | |
|---|---|---|---|
| 4,857,636 | 8/1989 | Hsia | 530/385 |
| 5,250,665 | 10/1993 | Kluger | 530/385 |
| 5,336,493 | 8/1994 | Poznansky et al. | 424/94.2 |
| 5,352,773 | 10/1994 | Kandler et al. | 530/385 |

OTHER PUBLICATIONS

"Hemoglobin-Based Red Cell Substitutes", Robert M. Winslow, MD, (A book), The John's Hopkins University Press, 1992.

"Blood Substitutes and Oxygen Carriers" Thomas M. S. Chang (Editor), (A book), published by Marcel Dekker, New York, 1992.

Halliwell et al. "Free Radicals, Antioxidants, & Human Disease: Where Are We Now?" J. Lab. Clin. Med. 119(6) 598–620 1992.

Reilly et al. "Pharmacologic Approach to Tissue Injury Mediated by Free Radicals & Other Reactive Oxygen Metabolites" Am J. Surg. 161 488–503 1991.

*Primary Examiner*—David Guzo
*Assistant Examiner*—Nancy J. Degen
*Attorney, Agent, or Firm*—Ridout & Maybee

[57] ABSTRACT

Crosslinked hemoglobin preparations having chemically bound thereto superoxide dismutase (SOD) and catalase are provided, for use as oxygen carrying rescusitative fluids, e.g. blood substitutes. The enzymes crosslinked to the hemoglobin effectively scavenge super oxide and hydrogen peroxide to improve the performance of the fluid in respect of ischemia-reperfusion injury risks.

8 Claims, 2 Drawing Sheets

HEMOGLOBIN-ENZYME COMPLEXES

FIELD OF THE INVENTION

This invention relates to acellular hemoglobin-based oxygen carriers and uses thereof. More particularly it relates to methods and compositions for improving the performance of such acellular hemoglobin-based oxygen carriers.

BACKGROUND AND BRIEF REFERENCE TO THE PRIOR ART

A cellular hemoglobin-based oxygen carriers show promise for use as blood substitutes. They are basically prepared by extracting hemoglobin from red blood cells, purifying it to a very high degree, intramolecularly crosslinking it to ensure that it maintains its basic tetrameric 64 kilodalton molecular size, optionally oligomerizing it to a higher molecular weight, and preparing an aqueous solution thereof at appropriate concentration. Prior art references disclosing such blood substitutes include U.S. Pat. No. 4,857,636 Hsia, U.S. Pat. No. 5,250,665 Kluger et. al, a book entitled *"Hemoglobin-based Red Cell Blood Substitutes"* edited by R. M. Winslow, John Hopkins University Press (1992), and a book entitled "Blood Substitutes and Oxygen Carriers", edited by Thomas M. S. Chang, Marcel Dekker, Publisher, New York (1992).

One of the primary fields in which such blood substitutes are required for use is in association with surgical procedures. The reintroduction of oxygen into an ischemic tissue or organ can cause ischemia-reperfusion injury. Such injuries are generally accepted to be associated with the presence of oxygen-derived free radicals. A desirable oxygen carrier is one that delivers oxygen effectively, and at the same time prevents the increase in the oxygen-derived free radicals. It is suspected that hemoglobin-based solutions when used in biological systems may lead to an increase in oxygen free radicals, and provide catalytic heme iron.

There are several mechanisms by which the generation of oxygen-derived free radicals can occur. In one mechanism, in the presence of superoxide and hydrogen peroxide, heme iron (bound and/or released) can drive fenton reactions generating highly reactive perferryl or hydroxyl reactions. In a second mechanism, heme groups can auto-oxidize and release superoxide. In a third mechanism, modified hemoglobins may stimulate phagocyte respiratory burst activity and increase arachidonic acid metabolism, leading to an increase in superoxide production.

Endogenous antioxidant enzymes, namely superoxide dismutase (SOD) and catalase, catalyze the breakdown of superoxide and hydrogen peroxide respectively. Although not all reported results are consistent, many reports have shown that SOD and/or catalase are effective in reducing reperfusion injury and other free radical-mediated injury processes.

It is an object of the present invention to provide a novel crosslinked hemoglobin based oxygen carrier.

It is a further object to provide such a novel carrier which utilizes the beneficial properties of at least one endogenous enzyme.

SUMMARY OF THE INVENTION

The present invention provides, from a first aspect, a novel complex of polymeric hemoglobin (by which term is meant hemoglobin intramolecularly crosslinked and having a molecular weight of 64 kd or higher) chemically bound to at least one endogenous enzyme selected from SOD and catalase. The complex is prepared by chemically reacting the hemoglobin with the enzyme in the presence of a chemical crosslinking reagent. The complex demonstrates activity, in vivo, to scavenge oxygen-derived free radicals.

DESCRIPTION OF THE PREFERRED EMBODIMENTS

Figure 1:
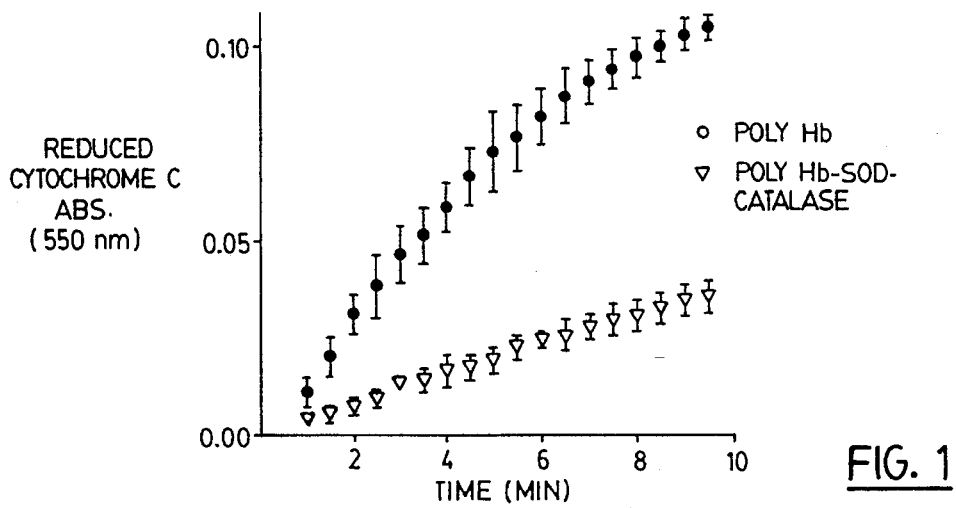
FIG. 1 and FIG. 2 are graphical presentations of the results of Example 1 below.

The preferred embodiment of the present invention utilizes both SOD and catalase in a complex with polyhemoglobin, preferably crosslinked therewith and prepared by reacting together polyhemoglobin, SOD and catalase in appropriate proportions, in the presence of a crosslinking agent for the hemoglobin. Such a complex is hereinafter referred to as PolyHb-SOD-catalase.

There is good reason to prefer a complex carrying both SOD and catalase instead of one or the other. The abnormal production of superoxide may be a significant mechanism in hemoglobin-induced oxidative stress. SOD eliminates superoxide, but in the process produces hydrogen peroxide. The use of catalase avoids the accumulation of hydrogen peroxide.

Chemically binding, e.g. crosslinking, the enzymes to the polyhemoglobin overcomes the problem of rapid removal of the free enzymes SOD and catalase from the circulation (10 and 20 minutes respectively). It also ensures that they will be located at sufficient proximity to the polyhemoglobin to provide the desired protection.

The complex of the present invention, PolyHb-SOD-catalase, is also useful in the preservation of donor organs, being stored extracorporeally awaiting transplant into a host. Anti-oxidant properties are required in preservative fluids for this purpose, and the complex of the invention meets these requirements.

In preparing the complex, any suitable inert crosslinking reagent previously reported as suitable for preparing crosslinked hemoglobin for use as an oxygen-carrying resuscitative fluid can be used, for example glutaraldehyde, diasprin derivatives, polyaldehydes including those derived from oxidative ring-opening of oligosaccharides, diphosphate esters, triphosphate esters, etc. The enzymes of interest have chemical groups similar to those on the globin chains of hemoglobin so that they will appropriately chemically bind to the hemoglobin as it crosslinks by reaction with the crosslinking reagent. The source of the hemoglobin may be outdated human blood or animal blood, e.g. bovine blood.

Relative amounts of polyhemoglobin, SOD and catalase in the complex according to the present invention can vary over wide limits, with the polyhemoglobin always constituting by far the major component. The total weight of the enzyme(s) is suitably in the approximate range of 0.1–10% based on the weight of the polyhemoglobin, and preferably in the approximate range 0.5–2.5%. When, as in the preferred embodiment, both SOD and catalase are chemically bound to the polyhemoglobin, the weight ratio of SOD to catalase is suitably from about 1:1 to 5:1 and preferably from about 1.5:1 to 2.5:1.

Crosslinking SOD and/or catalase with hemoglobin, in accordance with the present invention, helps prevent the formation of met-hemoglobin. This can occur by anti-oxidation of hemoglobin, or as a result of other oxidative processes of hemoglobin. Met-hemoglobin has the $Fe^{2+}$-heme molecules of hemoglobin oxidized to the $Fe^{3+}$ state, and does not transport oxygen.

Catalase and SOD, normally present in red blood cells, helps control the natural met-hemoglobin formation. During preparation of modified hemoglobin solutions, hemoglobin is subjected to several purification steps which remove these protective enzymes.

Thus the crosslinked SOD and/or catalase forming part of the complexes of the present invention can improve the suitability of these hemoglobin complexes as HBOCs by maintaining the oxygen-carrying chemical stat e. This is important in storage and preparation of modified hemoglobin. Further, the crosslinked enzymes may prevent the formation of met-hemoglobin under conditions of in vivo oxidative stress. They can prevent hemoglobin molecules themselves from aggravating oxidative stress.

DESCRIPTION OF THE SPECIFIC MOST PREFERRED EMBODIMENTS

The invention will be further described, for illustrative but non-limiting purposes, with reference to specific experimental examples, in which a preferred complex according to the invention is prepared and tested in vitro, to demonstrate its potential utility as an improved blood substitute.

Materials

Xanthine oxidase (20 µ/ml) and xanthine was obtained from ICN Biomedicalsl. Superoxide dismutase from bovine erythrocytes (EC1.15.1.1, 3000 units/mg stated activity) and catalase from beef liver (EC1.11.1.6, 65,000 units/mg stated activity) were purchased from Boehringer Mannheim. Purified bovine hemoglobin was used. Cytochrome C from horse heart (type III), 4-amino antipyrine horse radish peroxidase type IV (EC1.11.1.7), ferrozine (0.85%), and the iron standard (500 g/dl) were obtained from Sigma. The hemoglobin assay kit was purchased from Stan Bio Labs. All other reagents were of analytical grade.

Poly hemoglobin (PolyHb) was prepared by the method described in "*Appl. Biochem. Biotechnol.*", 10, 133–141, (1984), by Kippert, P. E.; and Chang, T. M. S.

EXAMPLE 1—Preparation of PolyHb-SOD-Catalase

Bovine hemoglobin (110 mg/ml), SOD (2 mg/ml) and catalase (20 mg/ml) were mixed in 0.1M sodium phosphate buffer, pH 7.6 with the final ratio (as mg/ml) of Hb:SOD:catalase of 55:0.5:0.25. Following the addition of an initial amount of lysine-HCl (0.12 ml of 1.3M/g Hb), gluteraldehyde (0.5 ml 0.5M/g Hb) was added to crosslink the protein mixture. The reaction was allowed to proceed for 1.5–2 hours before being stopped by addition of excess lysine (0.78 ml of 2.0M/g Hb). The resulting mixture was dialysed against Ringer's solution then filtered through a 0.2 µm Nalgrene filter. The hemoglobin concentration was measured. Molecular weight distribution analysis and degree of polymerization were performed using gel filtration chromatography on a Sephadex G-200 column equilibrated with 0.1M Tris-HCl, pH 7.5.

The molecular weight distributions were the same for Poly Hb and PolyHb-SOD-catalase. About 70% of the molecules were eluted in the molecular weight range greater than 600 kd, about 15% in the region 600 kd–66 kd, and the remaining eluted around 66 kd. The ratio of hemoglobin to SOD and catalase (as mg/ml) was 1:0.009:0.0045. Thus the added enzymes did not significantly affect the molecular weight distribution.

EXAMPLE 2—Scavenging of Superoxide

Experiments were designed to determine whether PolyHb-SOD-catalase eliminated enzymatically-generated superoxide. The experiments were based on the reduction of cytochrome c by superoxide, as described by Crapo, J. D., McCord, J. M and Fridovich, L, in "Methods of Enzymology," 52, 382–387, (1978), but slightly modified. Each reaction mixture (3 ml) contains xanthine (50 µM), cytochrome c (10 µM), and catalase (10 nM) in 50 mM potassium phosphate buffer containing 0.1 mM EDTA at pH 7.8. Free catalase was added to reaction mixtures to prevent interference resulting from the accumulation of hydrogen peroxide. Each reaction mixture also contains either PolyHb (5 µM) or polyHb-SOD-Catalase (5 µm). Addition of 10 µl xanthine oxidase (4 U/ml) starts the reaction at 22° C. The rate of cytochrome c reduction was monitored at 550 mm with a Perkin Elmer Lambda 4B Spectrophotometer. The molar extinction coefficient used for reduced cytochrome c was $2.1 \times 10^4 M^{-1} cm^{-1}$.

The results are shown in FIG. 1. The presence of SOD activity is indicated by an inhibited rate of cytochrome c reduction. The initial rate of cytochrome c reduction was 0.56–0.08 nmoles cyt. c/min for PolyHb-SOD-catalase compared to 2.13–0.26 nmoles for polyHb. Interference due to the presence of hemoglobin components in the reaction mixture was ruled out, since the rate of reduction in PlyHb mixtures was similar to the reduction rate in buffer alone.

Figure 2:
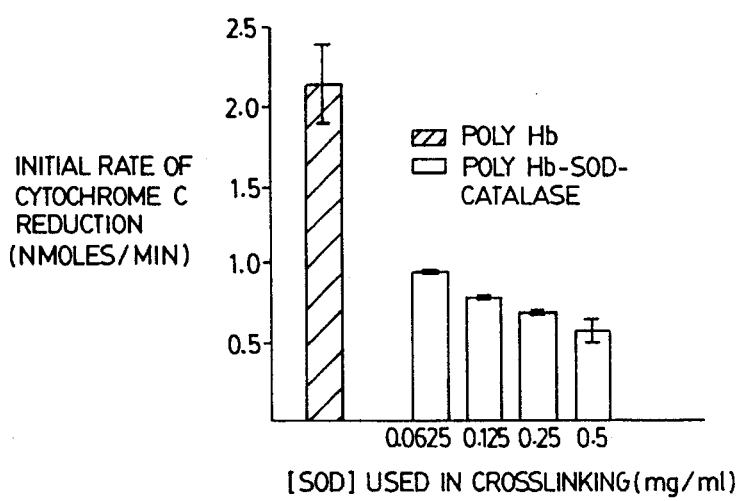

A series of similar experiments using a complex loaded with different amounts of SOD was also conducted. It was found that the superoxide scavenging activity of the polymerized solution varies with the SOD concentration used during crosslinking, as illustrated on FIG. 2.

EXAMPLE 3—Scavenging of Hydrogen Peroxide

Experiments were conducted to determine whether PolyHb-SOD-catalase eliminates reagent hydrogen peroxide. The method was a slightly modified version of that described by Frew, J. E; Jones, P; and Scholes, G; "*Anal. Chim. Acta.*", 155, 139–43 (1983). Reaction volumes (3 ml) containing the horseradish peroxidase/4-aminoantipyrine/phenol reagent solution (1.2 ml), PolyHb or PolyHb-SOD-catalase (5 µM), water and hydrogen peroxide were prepared. Identical mixtures containing additional water instead of hydrogen peroxide served as blanks. After allowing the mixture to stand for three minutes at 22° C., the absorbance at 505 nm was recorded. Hydrogen peroxide and the reagent solution participate in a peroxidase-catalysed reaction to form a dye which can be measured at this wavelength.

In reaction mixtures containing PolyHb-SOD-catalase, only about 20% of the added hydrogen peroxide was recoverable at each concentration studied, whereas more than 90% was detectable in PolyHb mixtures. With increasing hydrogen peroxide concentrations, reactions between PolyHb itself and hydrogen peroxide became more evident. The hydrogen peroxide scavenging activity of PolyHb-SOD-catalase varies with the catalase concentration used during the crosslinking.

EXAMPLE 4—Monitoring Absorbance Spectra Following Oxidative Challenge

Hydrogen peroxide was added to PolyHb (10 µM) or PolyHb-SOD-catalase (10 µM), and the absorbance spectra (450–700 nm) were recorded over time, to monitor the reactions of oxygen free radicals with the hemoglobin components of the cross-linked solutions. Results obtained from reactions with hydrogen peroxide and PolyHb showed that the heme moieties were rapidly degraded with excess hydrogen peroxide. In contrast, the absorbance spectra of PolyHb-SOD-catalase during similar experiments were minimally affected, indicating that these reactions are minimized due to the elimination of hydrogen peroxide.

Figure 4A:
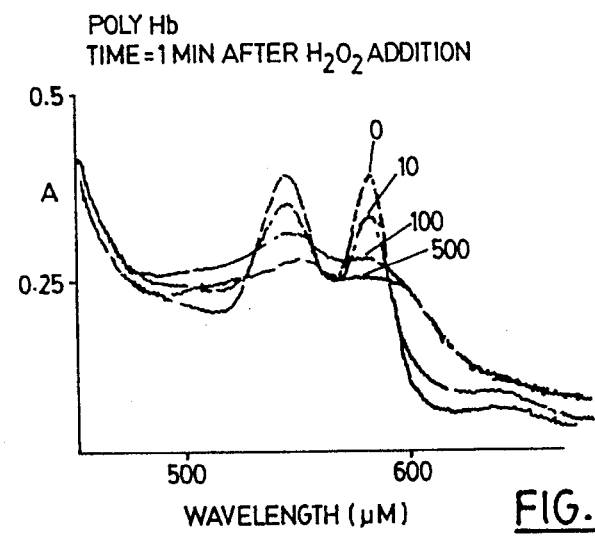
FIGS. 4A–4D are absorbance spectra of the products produced according to Example 4 below.
Figure 4B:
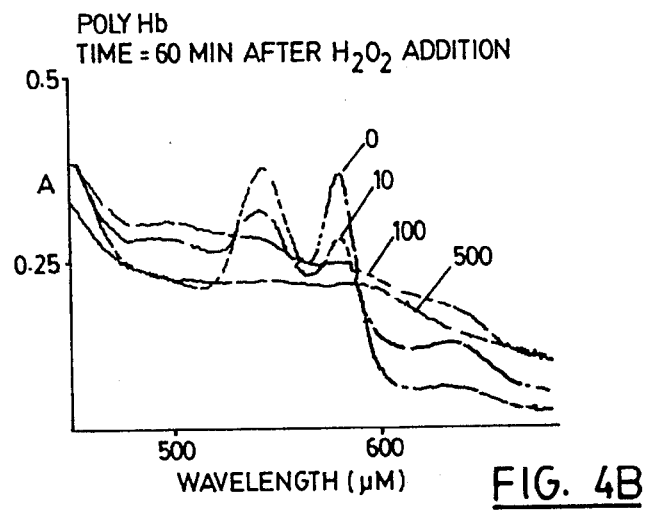
Figure 4C:
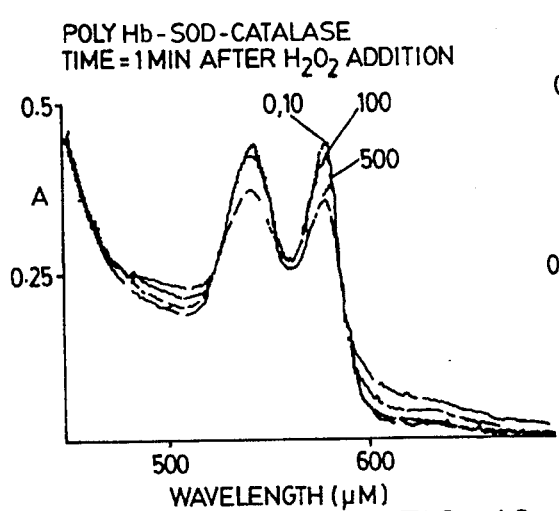
Figure 4D:
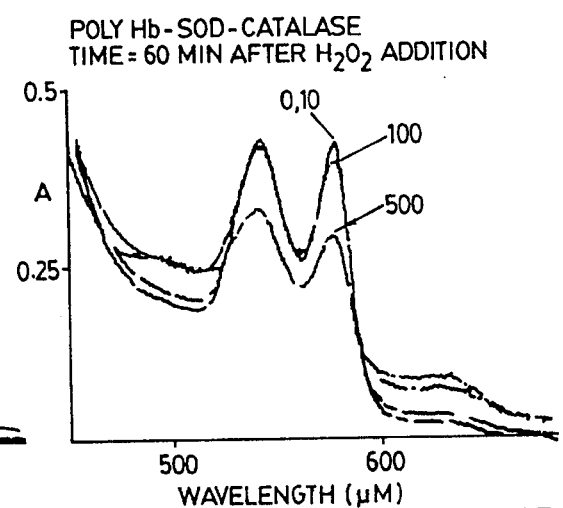

The absorbance spectra are reproduced herein as FIGS. 4A–4D. Each figure shows four different spectra, obtained respectively following addition to the hemoglobin material of 0, 10, 100 and 500 µM of hydrogen peroxide. The spectra FIG. 4A are taken one minute after the addition of the hydrogen peroxide to the crosslinked polyHb, carrying no enzymes. Those of FIG. 4B are taken 60 minutes thereafter. The corresponding spectra after $H_2O_2$ addition to the complex of the invention prepared according to Example 1 are FIG. 4C and FIG. 4D. The drastic change in the hemoglobin demonstrated in FIGS. 4A and 4B is in clear contrast to the very small changes demonstrated in FIGS. 4C and 4D.

Similar results were recorded following oxidative challenge with exogenous superoxide via xanthine/xanthine oxidase. It was observed, from the spectra recorded in the absence of hydrogen peroxide, that the PolyHb solution contained higher starting materials of methemoglobin compared to PolyHb-SOD-catalase solutions, indicating that PolyHb-SOD-catalase has protection against oxidation during the preparation and/or storage of modified hemoglobin solutions.

EXAMPLE 5—Iron Measurement

These measurements were conducted according to the method of Carter, P, "*Anal. Biochem.,*", 40, 450–458 (1971).

PolyHb or PolyHb-SOD-catalase (15 µM) was incubated in hydrogen peroxide (total volume 0.5 ml) for 60 minutes at 37° C. Catalase was added to remove residual hydrogen peroxide, then ascorbic acid (0.5 ml of 0.02%) was added and mixed for 5 mins. Trichloroacetic acid (0.5 ml of 20%) was then added to precipitate protein. The 1.5 ml mixture was centrifuged, and the supernatant (1 ml) was added to ammonium acetate buffer (0.45 ml) and ferrozine reagent (50 µl) The iron colour complex was measured at 560 nm. The amount of iron released was calculated by measuring the absorbance of an iron standard (500 µd/dl) (0.5 ml), treated as described above, against blank (0.5 ml water).

Figure 3:
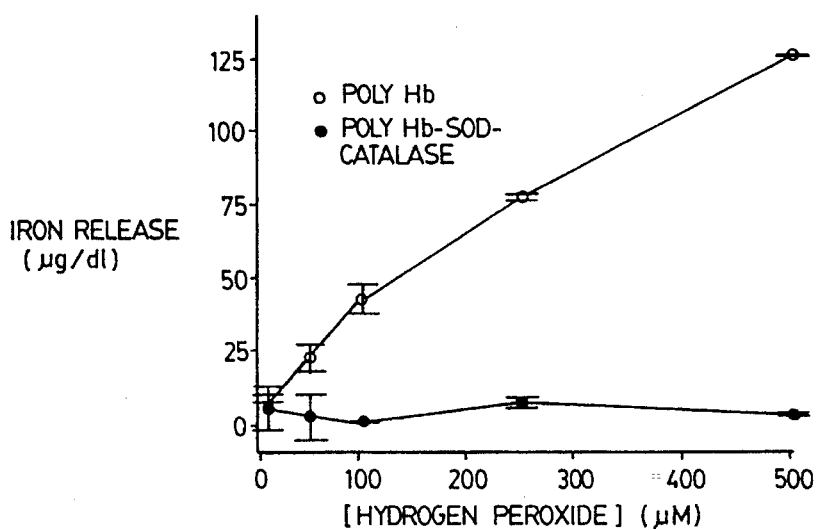
FIG. 3 is a graphical presentation of the results of Example 5 below.

The results are shown in FIG. 3. With hydrogen peroxide additions of 10–500 µm, it is estimated that from 2 to 37% of the total iron in PolyHb (15 µm) was "freed" and made detectable by ferrozine assay. Over the same hydrogen peroxide concentrations, less than 1% was released from PolyHb-SOD-catalase. It was also found that the catalase concentration used during crosslinking directly affects the amount of iron released during hydrogen peroxide incubation.

Preliminary animal, in vivo experiments have also revealed that the PolyHb-SOD-catalase complex of the present invention reduces the formation of hydroxyl radical, based on the measurement of salicylate hydroxylation products, in a simulated model of ischemia-reperfusion injury.

What we claim is:

1. A complex of intramolecularly and/or intermolecularly crosslinked hemoglobin, and endogenous enzymes chemically bonded thereto, said endogenous enzymes being superoxide dismutase (SOD) and catalase, the molecular weight of said complex being at least 64 kilodaltons, the oxygen-carrying crosslinked hemoglobin component of the the complex comprising about 90–99.9% by weight thereof and the total weight of bound enzymes in the complex comprising about 0.1–10% by weight thereof.

2. The complex of claim 1 wherein the SOD and the catalase are chemically bound to the hemoglobin by crosslinking thereto by chemical reaction of the hemoglobin, SOD and catalase with a crosslinking reagent.

3. The complex of claim 2 wherein the total bound enzyme is from about 0.5–2.5 weight %, based on the weight of the hemoglobin.

4. The complex of claim 3 wherein the weight ratio of SOD to catalase is from about 1.5:1 to 2.5:1.

5. The complex of claim 2 wherein the weight ratio of SOD to catalase is from about 1:1 to 5:1.

6. The complex of claim 5 wherein the complex is crosslinked with a hemoglobin crosslinking reagent selected from the group consisting of glutaraldehyde, diaspirin derivatives, polyaldehydes derived from oxidative ring-opening of oligosaccharides, diphosphate esters, and triphosphate esters.

7. An oxygen transporting rescusitative fluid useful for administration to a mammal as a blood substitute, comprising an aqueous solution of a complex as defined in claim 1.

8. A process of preparing a crosslinked hemoglobin complex having bound thereto the enzyme superoxide dismutase (SOD) and the enzyme catalase (polyHb-SOD-catalase), the crosslinked hemoglobin oxygen carrying component of the complex comprising about 90–99.9% by weight thereof and the total amount of said enzymes bound in the complex being from about 0.1 to about 10 weight % thereof, which comprises reacting purified, uncrosslinked hemoglobin in aqueous solution with appropriate amounts of SOD and catalase to yield a complex having said total amount of said enzymes bound therein, and with a hemoglobin crosslinking reagent, quenching the reaction at the appropriate end-point by addition to the reaction mixture of a reagent reactive with the crosslinking reagent, and recovering the PolyHb-SOD-catalase crosslinked complex so formed.

* * * * *